(12) United States Patent
Couillard et al.

(10) Patent No.: US 7,422,685 B2
(45) Date of Patent: Sep. 9, 2008

(54) METHOD AND DEVICE FOR SEPARATING CONSTITUENTS OF A LIQUID CHARGE BY MEANS OF LIQUID-LIQUID CENTRIFUGE CHROMATOGRAPHY

(75) Inventors: François Couillard, 5 rue des Bernaches, 56860 Sene (FR); Alain Foucault, Saint Nazaire (FR); Daniel Durand, Rueil Malmaison (FR)

(73) Assignees: Institut Francais du Petrole, Rueil Malmaison Cedex (FR); Francois Couillard, Sene (FR)

( * ) Notice: Subject to any disclaimer, the term of this patent is extended or adjusted under 35 U.S.C. 154(b) by 273 days.

(21) Appl. No.: 10/562,726

(22) PCT Filed: Jun. 28, 2004

(86) PCT No.: PCT/FR2004/001653

§ 371 (c)(1),
(2), (4) Date: Apr. 14, 2006

(87) PCT Pub. No.: WO2005/011835

PCT Pub. Date: Feb. 10, 2005

(65) Prior Publication Data

US 2006/0243665 A1  Nov. 2, 2006

(30) Foreign Application Priority Data

Jul. 2, 2003  (FR) .................................. 03 08076

(51) Int. Cl.
*B01D 15/08* (2006.01)
(52) U.S. Cl. .................... 210/198.2; 210/635; 210/657

(58) Field of Classification Search ................. 210/635, 210/656, 657, 198.2
See application file for complete search history.

(56) References Cited

U.S. PATENT DOCUMENTS 4,051,025 A * 9/1977 Ito ............................. 210/635

(Continued)

FOREIGN PATENT DOCUMENTS

DE    31 30 967    2/1983

(Continued)

OTHER PUBLICATIONS

Den Hollander J. L. et al.: "Centrifugal partition chromatographic reaction for the production of chiral amino acids" Journal of Chromatography B: Biomedical Sciences & Applications, Elsevier Publishers, vol. 711, pp. 223-235.

*Primary Examiner*—Ernest G Therkorn
(74) *Attorney, Agent, or Firm*—Antonelli, Terry, Stout & Kraus, LLP.

(57) ABSTRACT

The invention relates to a method for separating constituents of a liquid feed by liquid-liquid centrifugal chromatography and to a device for implementing it. Constituents (A, B) having different partition coefficients such that they are respectively carried along at unequal velocities by a light solvent (1) and a heavier solvent (L), the feed is continuously injected at an intermediate point of a separation column (col), successive cycles comprising alternately a heavy solvent injection stage and a light solvent injection stage are carried out respectively at the two ends of the column consisting of the interconnection in series of at least one set of separation cells, and the separated solvents (FA, FB) are collected during each one of said stages at the column ends opposite the solvent injection points.

2 Claims, 3 Drawing Sheets

U.S. PATENT DOCUMENTS

| | | | |
|---|---|---|---|
| 4,551,251 A * | 11/1985 | Kolobow et al. | 210/635 |
| 4,632,762 A * | 12/1986 | Ramsland | 210/657 |
| 4,857,187 A * | 8/1989 | Ito | 210/198.2 |
| 4,877,523 A * | 10/1989 | Nunogaki | 210/198.2 |
| 4,900,435 A | 2/1990 | Anderson | |
| 4,968,428 A * | 11/1990 | Nunogaki | 210/635 |
| 6,537,452 B1 * | 3/2003 | de La Poype et al. | 210/198.2 |
| 6,576,137 B1 * | 6/2003 | Ma | 210/657 |
| 6,913,692 B2 * | 7/2005 | Margraff et al. | 210/198.2 |
| 2006/0243665 A1 * | 11/2006 | Couillard et al. | 210/635 |

FOREIGN PATENT DOCUMENTS

FR           2417340           9/1979

* cited by examiner

METHOD AND DEVICE FOR SEPARATING CONSTITUENTS OF A LIQUID CHARGE BY MEANS OF LIQUID-LIQUID CENTRIFUGE CHROMATOGRAPHY

FIELD OF THE INVENTION

The present invention relates to a method for separating constituents of a liquid feed by liquid-liquid centrifugal chromatography and to a device for implementing it.

BACKGROUND OF THE INVENTION

A known technique for separating constituents of a mixture, referred to as simulated moving bed (SMB) or simulated countercurrent (SCC) technique, consists in passing the mixture into a set of columns arranged in series and comprising each beds filled with an adsorbent. A complex assembly of pumps, lines and valves makes it possible to establish through the beds a fluid circulation allowing injection of a feed from which at least one constituent is to be separated and of an eluent containing chiefly the desorbent, or withdrawal of an extract containing chiefly the preferably adsorbed constituent or of a raffinate mainly consisting of the least preferably adsorbed elements. Such a system is for example described in patent FR-2,762,793.

It is not possible in a SCC to circulate the solid phase. It is simulated by means of a complex set of valves and pumps controlled according to complicated algorithms. Periodic replacement of the solid phases in the columns is extremely costly and requires relatively long production stops. This type of system is difficult to manage because of the complexity thereof. Its maintenance is also heavy.

Another known technique for separating constituents A and B in solution in a liquid mixture consists in injecting it into a "chromatographic column" subjected to a centrifugal force, which is designed to allow one of the liquid phases to be percolated through the other liquid phase and vice versa (chromatography referred to as CCC or CPC).

In practice, as shown notably in patents FR-2,791,578, U.S. Pat. No. 4,551,251, U.S. Pat. No. 4,877,523 or U.S. Pat. No. 4,857,187, this type of system comprises one or more piles of disks D driven in rotation (see FIG. 4). Each one comprises in the thickness thereof and over its entire periphery a succession of cells CE laid out in a radial or oblique direction and arranged in series by a set of circuits of fine winding lines L at the ends of each cell. The circuits of all the disks communicate with one another. The cells and their communication circuits are filled with a stationary liquid phase kept in place by the centrifugal force and another mobile liquid phase that percolates through the stationary phase.

SUMMARY OF THE INVENTION

The method according to the invention allows separation of the constituents of a feed in liquid solution of at least two constituents of different partition coefficients such that they are carried along at unequal velocities respectively by a light solvent and by a heavier solvent, in a device comprising at least one liquid-liquid centrifugal chromatographic column consisting of the interconnection in series of at least one chain of separation cells.

The method is essentially characterized in that it comprises:

injecting the feed at an intermediate point of the chain of cells, and carrying out alternating cycles of two stages, with a first stage during a first time interval wherein a lighter solvent is injected through a first end of the device and a first constituent is collected at a second end of the device, and a second stage during a second time interval wherein a heavier solvent is injected through the second end of the device and a second constituent is collected at the first end.

Preferably, the respective durations of the first and second stages and/or the rates of injection of the lighter and of the heavier solvent are adjusted according to the constituents of the mixture so as to obtain optimum separation.

According to an embodiment, several cascade separations are performed to isolate from one another the various constituents of a mixture made up of more than two constituents.

This embodiment applies for example to the separation of two optical isomers with injection into a first device of a feed comprising the optical isomers and a chiral selector to obtain a first isomer on the one hand and a mixture of a second isomer and of chiral selector on the other hand, then injection of this mixture from the first device into a second device suited to separate the second isomer and the chiral selector.

The device according to the invention allows separation of the constituents of a feed in liquid solution of at least two constituents having different partition coefficients such that they are carried along at unequal velocities respectively by a lighter solvent and a heavier solvent. It comprises at least one liquid-liquid centrifugal chromatographic column consisting of the interconnection in series of at least one chain of separation cells. Each column is associated with a first pump for injecting the feed at an intermediate point of the chain of cells, a first valve connecting a first end of the column to a first vessel for collecting a first constituent (FA) or to a second pump for injecting a first solvent (L), a second valve (V2) connecting a second end of the column to a second vessel for collecting a second constituent (FB) or to a third pump (P3) for injecting a second solvent (1), alternating valves (V1, V2) switching means so as to switch alternately from a first stage with injection of the first solvent (L) and reception of the separated second constituent (FB) to a second stage with injection of the second solvent (1) and reception of the separated first constituent (FA), and means for controlling the pump flow rate.

According to an embodiment, the device comprises for example two cascade separation columns for separating the constituents of a mixture comprising at least three different constituents.

The device is also suited for continuous as well as discontinuous feed injection.

BRIEF DESCRIPTION OF THE FIGURES

Other features and advantages of the method and of the device according to the invention will be clear from reading the description hereafter of an embodiment given by way of non limitative example, with reference to the accompanying figures wherein.

DETAILED DESCRIPTION

The system essentially comprises (FIGS. 1, 2) at least one liquid-liquid centrifugal chromatographic column (Col) subjected to centrifugation designed to separate a mixture (A, B) into its two constituents A and B. At an intermediate point of the column, a pump P1 injects liquid mixture (A, B) to be separated continuously or discontinuously.

At a first end E1, the column is connected via a first valve V1 either to a first vessel FA for collecting first constituent A or to an inlet communicating through an injection pump P2 with a vessel containing a heavy solvent L. At its opposite end E2, the column is connected via a second valve V2 either to an outlet communicating with another vessel FB for collecting constituent B or to an inlet communicating through an injection pump P2 with a vessel containing a light solvent 1.

Figure 1:
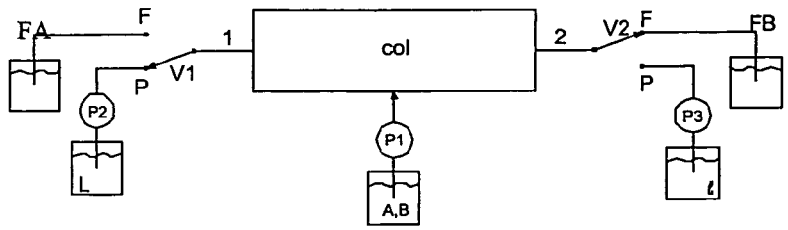
FIG. 1 diagrammatically shows, in a first cyclic operating stage, a separation unit with a separation column and associated circulation means where the mixture to be separated is injected at an intermediate point in accordance with the method of the invention, FIG. 2 diagrammatically shows the same unit in a second cyclic operating stage.
Figure 2:
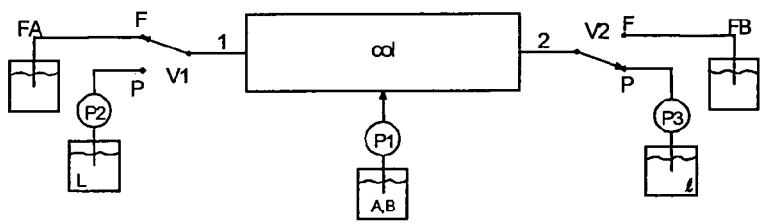

In the embodiment illustrated in FIGS. 1, 2, constituents A and B are considered to have partition coefficients such that B is carried along more rapidly than A by heavy solvent L and A is carried along more rapidly than B by light solvent 1.

In the first stage (FIG. 1) of duration $t_1$, pump P2 pumps during some time heavy solvent L which is then in a "mobile phase" situation, whereas light solvent 1 is in the device in a stationary phase situation.

In the second stage (FIG. 2) of duration $t_2$, pump P3 pumps during some time light solvent 1 which is then in a "mobile phase" situation, whereas heavy solvent L is in the device in a stationary phase situation.

After continuous injection of sample (A, B) by means of pump P1 and periodic switching of valves V1 and V2, thus alternately switching from the connection mode of FIG. 1 to that of FIG. 2, A ends up in vessel FA and B in vessel FB.

Figure 3:
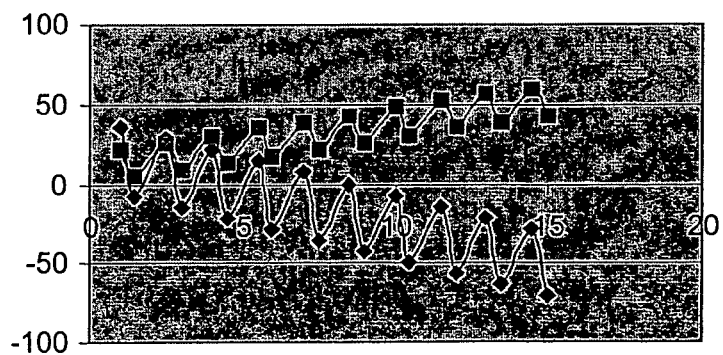
FIG. 3 illustrates, by way of example, the progressive separation as a function of time of the elements of a mixture injected at a given time into a 200-cell separation unit, under the action of the cyclic stages diagrammatically shown in FIGS. 1, 2.

This separation phenomenon is illustrated in FIG. 3 where a small amount of a mixture A, B was injected, at a given time and during a limited time interval, in the middle of a column with 200 interconnected cells for example. The separation phenomenon is observed with constituent A (grey) moving towards one end of the column and the other constituent B (black) moving towards the opposite end. It can be clearly seen in FIG. 3 that A and B are shuttled between the cells upon each cycle, which amounts to artificially lengthening the circulation distance. Everything goes on as though the number of cells had been increased.

Durations $t_1$ and $t_2$ and the injected solvent flow rates can be varied to obtain fast divergence of the constituents towards the opposite ends of the column (as shown in FIG. 3).

Of course, if mixture A, B is injected continuously, constituents A and B are also collected continuously.

In the device according to the invention, filling of the two liquid phases requires about ten minutes and, as long as the production type is not changed, there is no need to stop it.

The liquid phases are considerably less expensive than the solid phases used in SMB type separation systems. For the same production volume, the mobile phase consumption is reduced by a factor of the order of 10 with the device described.

Figure 4:
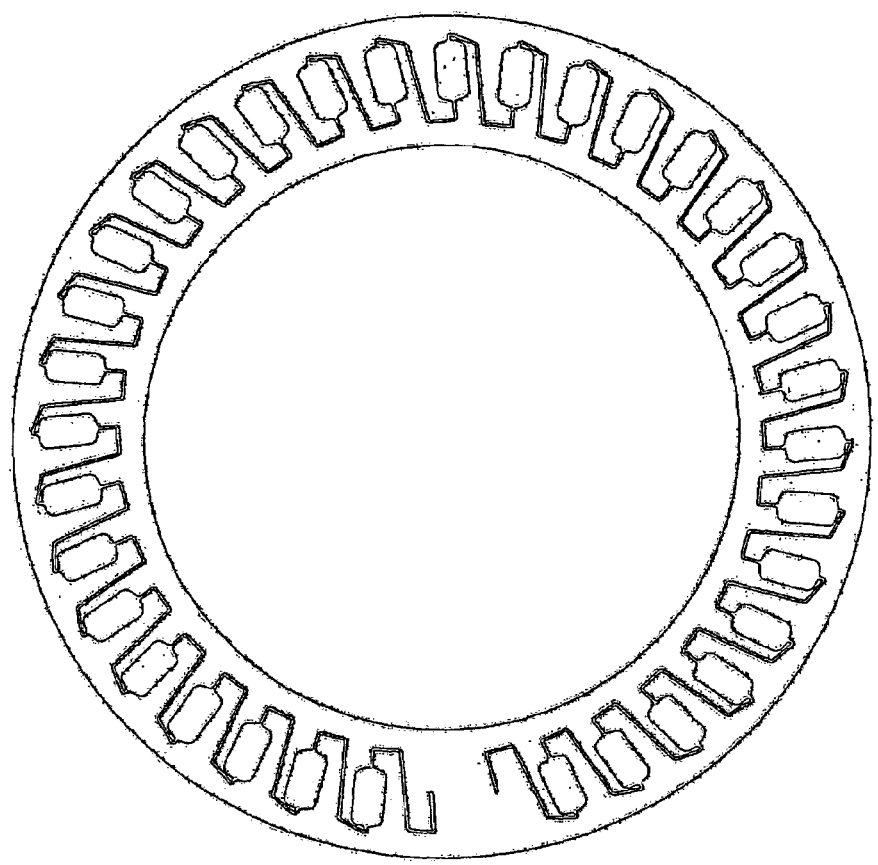
FIG. 4 shows an example of a column (or separation column fraction) in form of a disk subjected to centrifugation and comprising, over the entire periphery thereof, radial cells interconnected in series through which the constituents to be separated and the solvents circulate.
Figure 5:
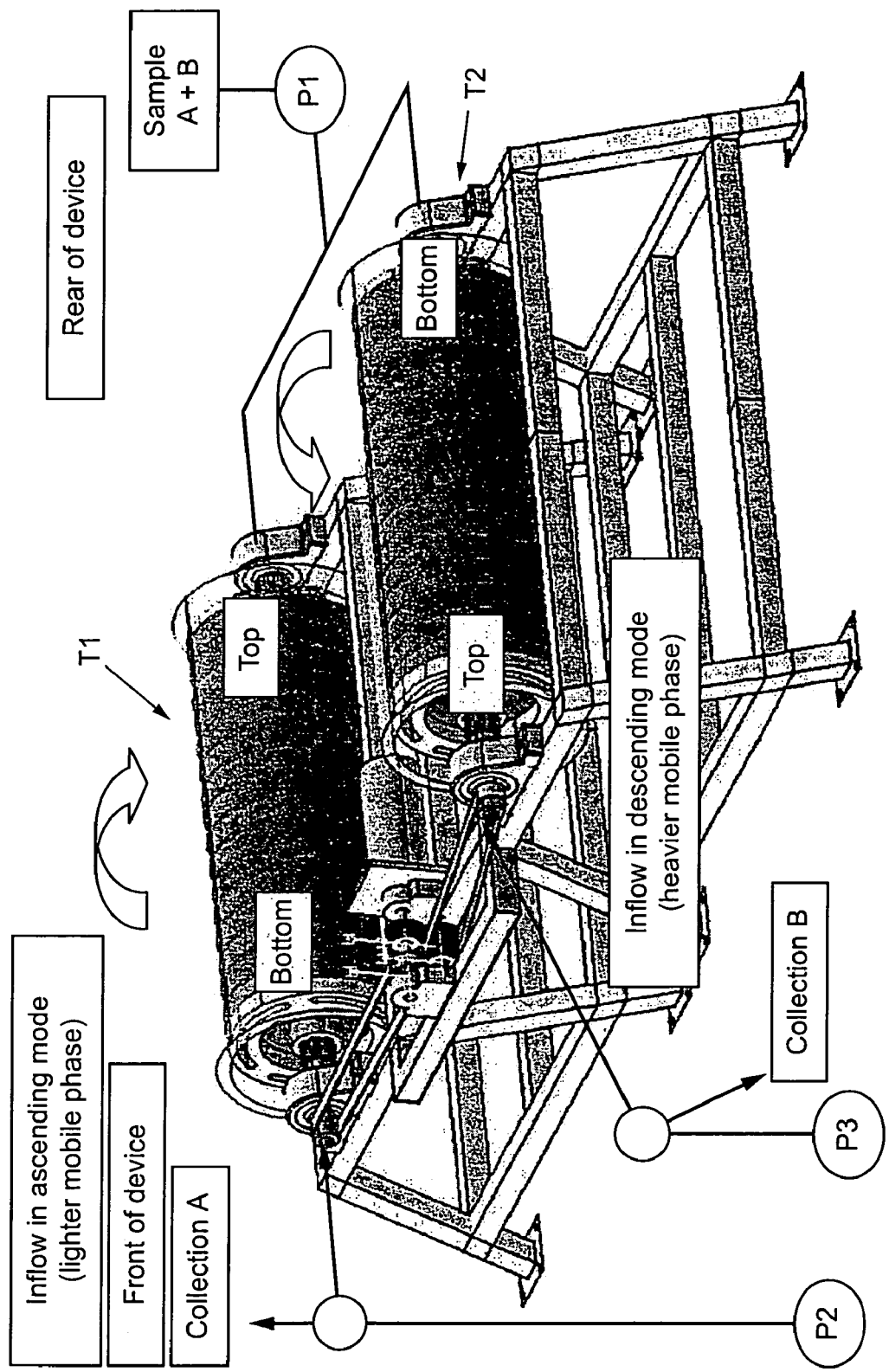
FIG. 5 shows an example of layout of two multi-disk separation sets subjected to centrifugation and interconnected in series, with injection of the mixture in the intermediate circuit connecting them, and FIG. 6 diagrammatically shows the cascade connection of separation sets allowing in some cases separation of a mixture comprising more than two constituents.

In the example of FIG. 5, the system comprises two parallel drums T1, T2 consisting each of a pile of disks as shown in FIG. 4 and driven in rotation. These two drums are connected in series. They can be rotated in the same direction or, as shown here, in opposite directions if the series interconnection circuits can be simplified thereby. The mixture is injected through pump P1 at an intermediate point on the line connecting them. Pump P2 is connected to the inlet of drum T1 in ascending mode (lighter mobile phase) and pump P3 is connected to the inlet of drum T2 in descending mode (heavier mobile phase).

It is clear that the intermediate point of injection of the mixture into the column can be selected wherever it is considered to be best, considering the effective partition coefficients of the constituents of the mixture.

Figure 6:
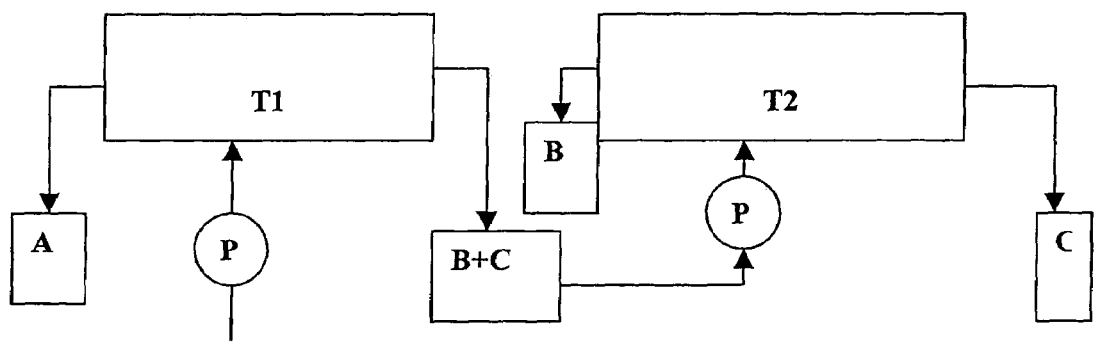

The separation system with several units of FIG. 6 allows to obtain cascade separations. If the initial mixture comprises three constituents A, B, C such that the first unit is suited to separate A on the one hand and B, C on the other hand, it is possible, after the first separation, to inject the remaining mixture B, C into a second separation unit and to obtain separation of constituents B and C.

It is advantageous for example in the case where two optical isomers are to be separated. A chiral selector is therefore usually added thereto. As known to the man skilled in the art, this allows to separately obtain, at the respective outlets of the first unit, a first isomer and the second isomer mixed with the chiral selector. If the remaining mixture of second isomer and chiral selector is injected into the second separation unit, the chiral selector can then be entirely recovered, which is very advantageous considering its high cost.

The two tables hereafter sum up the advantages of the method according to the invention (referred to as CPCPC), the first one in relation to conventional liquid-liquid centrifugal chromatography methods, and the second in relation to SMB type separation systems.

|  | Conventional CPC (and CCC) | CPCPC |
|---|---|---|
| Injection | Finite volume of A, B injected at one end of the "chromatographic column" | Continuous injection of A, B at a point located between the ends of the "chromatographic column" |
| Elution | Ascending mode or descending mode, or dual mode, i.e. a single cycle of the two modes | Alternating elution in the two modes, with a frequency Φ defined by the operator |
| Fractions collected | Fractions collected at the end of the "chromatographic column" opposite the injection end, or in dual mode successively at each end, corresponding to the single cycle of modes selected | Fractions collected at the two ends of the "chromatographic column", alternately with a frequency Φ |
| Two-phase systems | Identical for both techniques | |
| Filling of the "chromatographic column" | Generally stationary phase first, then equilibrium with the mobile phase before or after injection | Simultaneous filling with the two phases according to a ratio defined by the operator |

-continued

|  | SMB | CPCPC |
|---|---|---|
| Injection | Finite volume of A, B injected at one end of the "chromatographic column" | Continuous injection of A, B at a point located between the ends of the "chromatographic column" |
| Elution | Ascending mode or descending mode, or dual mode, i.e. a single cycle of the two modes | Alternating elution in the two modes, with a frequency Φ defined by the operator |
| Fractions collected | Fractions collected at the end of the "chromatographic column" opposite the injection end, or in dual mode successively at each end, corresponding to the single cycle of modes selected | Fractions collected at the two ends of the "chromatographic column", alternately with a frequency Φ |
| Two-phase systems | Identical for both techniques | |
| Filling of the "chromatographic column" | Generally stationary phase first, then equilibrium with the mobile phase before or after injection | Simultaneous filling with the two phases according to a ratio defined by the operator |

It can be noted that the separation system according to the invention substantially consumes 10 times less solvent than the SMB system.

It can also be noted that the feed can be injected continuously as well as discontinuously at an intermediate point of the column.

The invention claimed is:

1. A device for continuous separation of the constituents of a feed in liquid solution of at least two constituents (A, B) having different partition coefficients such that they are carried along at unequal velocities respectively by a lighter solvent and a heavier solvent, comprising at least one liquid-liquid centrifugal chromatographic column (col) consisting of the interconnection in series of at least one chain of separation cells (CE), characterized in that each column is associated with a first pump (P1) for injecting the feed at an intermediate point of the chain of cells, a first valve (V1) connecting a first end of the column to a first vessel for collecting a first constituent (FA) or to a second pump (P2) for injecting a first solvent (L), a second valve (V2) connecting a second end of the column to a second vessel for collecting a second constituent (FB) or to a third pump (P3) for injecting a second solvent (1), alternating valves (V1, V2) switching means so as to switch alternately from a first stage with injection of the first solvent (L) and reception of the separated second constituent (FB) to a second stage with injection of the second solvent (1) and reception of the separated first constituent (FA), and means for controlling the pump flow rate.

2. A device as claimed in claim 1, comprising at least two cascade separation columns arranged in cascade for separating constituents of a mixture comprising at least three different constituents.

* * * * *